(12) United States Patent
Yadegari et al.

(10) Patent No.: US 11,998,490 B2
(45) Date of Patent: Jun. 4, 2024

(54) ARM SUPPORT APPARATUS

(71) Applicant: Armery Medical Technologies Inc., London (CA)

(72) Inventors: Andrew Barbod Yadegari, North York (CA); Andrew Stephen McLellan, London (CA)

(73) Assignee: ARMERY MEDICAL TECHNOLOGIES INC., London (CA)

( * ) Notice: Subject to any disclaimer, the term of this patent is extended or adjusted under 35 U.S.C. 154(b) by 797 days.

(21) Appl. No.: 17/051,493

(22) PCT Filed: May 29, 2019

(86) PCT No.: PCT/CA2019/050727
§ 371 (c)(1),
(2) Date: Oct. 29, 2020

(87) PCT Pub. No.: WO2019/227210
PCT Pub. Date: Dec. 5, 2019

(65) Prior Publication Data
US 2022/0233384 A1    Jul. 28, 2022

Related U.S. Application Data

(60) Provisional application No. 62/836,811, filed on Apr. 22, 2019, provisional application No. 62/677,266, filed on May 29, 2018.

(30) Foreign Application Priority Data

May 29, 2018    (CA) ..................... 3006471

(51) Int. Cl.
*A61G 13/12*    (2006.01)
*A61B 6/04*    (2006.01)
(Continued)

(52) U.S. Cl.
CPC .......... *A61G 13/1235* (2013.01); *A61B 6/107* (2013.01); *A61B 6/0407* (2013.01);
(Continued)

(58) Field of Classification Search
CPC ............ A61G 13/1235; A61G 13/1205; A61G 13/124; A61G 13/0045; A61G 13/0036;
(Continued)

(56) References Cited

U.S. PATENT DOCUMENTS 2,933,738 A * 4/1960 Whelan ................ A47C 20/027
5/630
9,763,843 B2    9/2017 Crisco et al.
(Continued)

FOREIGN PATENT DOCUMENTS

| CA | 2912174 A1 | 1/2015 |
|---|---|---|
| CA | 3006471 A1 | 11/2019 |

(Continued)

OTHER PUBLICATIONS

International Preliminary Report on Patentability dated Dec. 10, 2020 in respect of PCT/CA2019/050727.
(Continued)

*Primary Examiner* — David R Hare
*Assistant Examiner* — Deborah Talitha Gedeon
(74) *Attorney, Agent, or Firm* — Bereskin & Parr LLP/S.E.N.C.R.L., s.r.l.

(57) ABSTRACT

An apparatus for supporting an arm of a human patient during a medical procedure can include a base, an arm pad, and barriers for shielding scatter radiation. A medial portion of the base can lie between the human patient and a table on which the human patient is supported. The arm pad can be positioned on a lateral portion of the base. A first barrier can be mounted to the base and can be positioned laterally intermediate the medial and lateral portions, the first barrier
(Continued)

extending upwardly from the base to above the arm pad. A second barrier can be mounted to the lateral portion of the base and extend downwardly. The arm pad can include a radiopaque panel that is horizontal.

20 Claims, 20 Drawing Sheets

(51) Int. Cl.
*A61B 6/10* (2006.01)
*A61G 13/00* (2006.01)

(52) U.S. Cl.
CPC ...... *A61G 13/0045* (2016.11); *A61G 13/1205* (2013.01); *A61G 13/124* (2013.01); *A61G 2210/50* (2013.01)

(58) Field of Classification Search
CPC .............. A61G 13/1255; A61G 13/126; A61G 2210/50; A61G 13/12; A61G 13/1265; A61G 13/127; A61G 13/1275; A61G 13/128; A61G 13/1285; A61G 13/129; A61G 13/1295; A61G 5/125; A61G 2200/54; A61G 7/075; A61B 6/107; A61B 6/04; A61B 6/0407; A61F 5/3723; A61F 5/0118; A61M 5/52

See application file for complete search history.

(56) References Cited

U.S. PATENT DOCUMENTS

| | | | |
|---|---|---|---|
| 2011/0184278 A1* | 7/2011 | Goff | A61B 6/04 128/877 |
| 2014/0316253 A1 | 10/2014 | Crisco et al. | |
| 2016/0038365 A1* | 2/2016 | Conner | A61B 6/0407 5/601 |
| 2016/0089295 A1* | 3/2016 | Panetta | A61G 15/12 128/845 |
| 2016/0317110 A1* | 11/2016 | Rees | G21F 3/00 |
| 2017/0042751 A1* | 2/2017 | Lassetter | A61G 13/1285 |

FOREIGN PATENT DOCUMENTS

| | | | | |
|---|---|---|---|---|
| CN | 107661116 A | | 2/2018 | |
| DE | 202008006049 U1 | | 8/2008 | |
| DE | 202010012488 U1 | | 11/2010 | |
| WO | WO-0015160 A1 | * | 3/2000 | ......... A61F 5/05866 |
| WO | 2015/012906 A1 | | 1/2015 | |
| WO | 2017/218871 A1 | | 12/2017 | |
| WO | 2019/227210 A1 | | 12/2019 | |

OTHER PUBLICATIONS

International Search Report and Written Opinion dated Aug. 20, 2019 in respect of PCT/CA2019/050727.

* cited by examiner

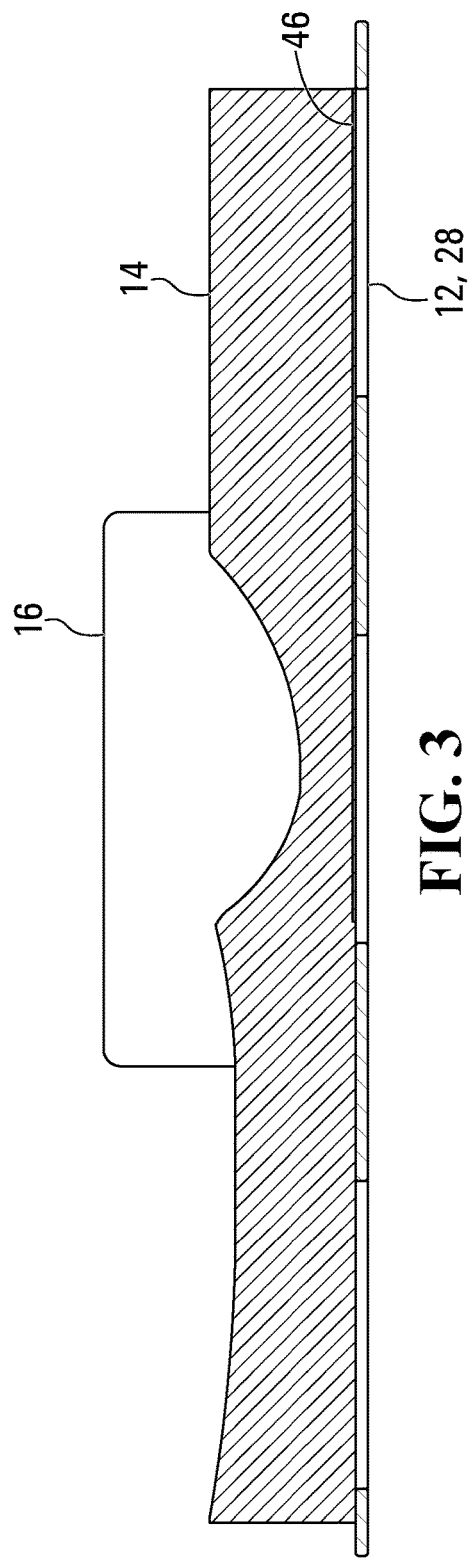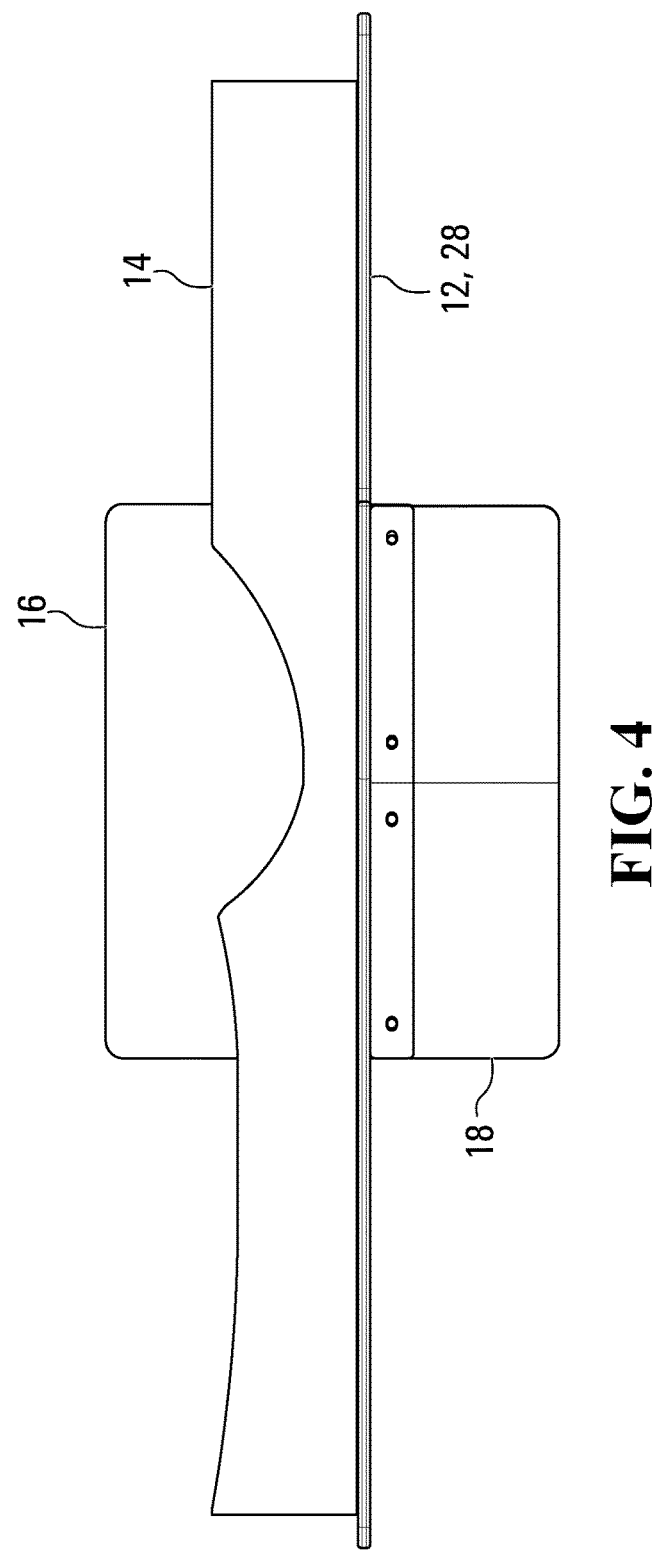

ARM SUPPORT APPARATUS

CROSS REFERENCE TO RELATED APPLICATIONS

This is a national stage application of International Application No. PCT/CA2019/050727 filed on May 29, 2019, which claims priority to U.S. Provisional Application No. 62/677,266 filed on May 29, 2018, Canadian Application No. 3,006,471 filed on May 29, 2018, and U.S. Provisional Application No. 62/836,811 filed on Apr. 22, 2019, and the entire contents of each are hereby incorporated herein by reference.

FIELD

The present disclosure relates generally to apparatuses for and methods of supporting a human patient's arm during medical procedures, and more particularly to gaining access to a human patient's radial artery during cardiac catheterization procedures.

BACKGROUND

The following paragraphs are not an admission that anything discussed in them is prior art or part of the knowledge of persons skilled in the art.

United States Publication No. 20160038365 describes systems and methods for left radial access, right room operation peripheral interventions that include left radial bases to stabilize a left arm of a cardiac patient across a midsagittal plane, transradiant right radial bases to position a right arm of the patient, and radiodense radiation reduction barriers located between the patient and a doctor.

U.S. Pat. No. 9,763,843 describes a medical apparatus for use in supporting a patient lying in a supine position during a radial cardiac catheterization procedure. More particularly, an arm board is described for use with a patient's arm during a radial cardiac catheterization procedure. The arm board has a base member having a substantially planar support surface on which the patient's arm can be stabilized during a catheterization procedure and at least one shield member affixed to the base member and extending away from the support surface. The base member has both a radiolucent portion and a radiopaque portion and the shield member is a radiopaque material, thereby reducing and/or eliminating a doctor's exposure to radiation during radial cardiac catheterization procedures without impairing the ability to obtain the necessary medical images.

INTRODUCTION

The following summary is intended to introduce the reader to various aspects of the applicant's teaching, but not to define any invention.

According to some aspects of the present disclosure, an apparatus for supporting an arm of a human patient during a medical procedure is disclosed. The apparatus can include: a base including a medial portion that is configured to lie between the human patient and a table on which the human patient is supported, and a lateral portion that extends laterally from the medial portion; an arm pad positioned on the lateral portion of the base, the arm pad extending longitudinally between first and second ends; a first barrier for shielding scatter radiation during the medical procedure, the first barrier mounted to the base and positioned laterally intermediate the medial and lateral portions thereof, the first barrier extending upwardly from the base to above the arm pad; and a second barrier for shielding scatter radiation during the medical procedure, the second barrier mounted to the lateral portion of the base and extending downwardly therefrom.

According to some aspects of the present disclosure, an apparatus can include: a base; a first barrier mounted to the base for shielding scatter radiation, the first barrier extending upwardly from the base; a second barrier mounted to the base for shielding scatter radiation, the second barrier extending downwardly from the base; and an arm pad on the base positioned laterally intermediate the first and second barriers, the arm pad including a proximal portion for supporting an arm of a human patient, and a central portion for supporting a hand of the arm.

According to some aspects of the present disclosure, a method of supporting an arm of a human patient is disclosed. The method can include: positioning a base to lie between the human patient and a table on which the human patient is supported, the base including a lateral portion that extends laterally from the table; placing the arm of the human patient on an arm pad that is positioned on the lateral portion of the base; shielding scatter radiation with a first barrier, the first barrier mounted to the base and positioned laterally intermediate the lateral portion and the human patient, the first barrier extending upwardly from the base to above the arm pad; and shielding scatter radiation with a second barrier, the second barrier mounted to the lateral portion of the base and extending downwardly therefrom.

Other aspects and features of the teachings disclosed herein will become apparent, to those ordinarily skilled in the art, upon review of the following description of the specific examples of the present disclosure.

BRIEF DESCRIPTION OF THE DRAWINGS

The drawings included herewith are for illustrating various examples of apparatuses and methods of the present disclosure and are not intended to limit the scope of what is taught in any way. In the drawings:

FIG. 3 is a side sectional view taken along line 3-3 in FIG. 2;

FIGS. 4 and 5 are side and end views, respectively, of the apparatus of FIG. 1;

DETAILED DESCRIPTION

Various apparatuses or methods will be described below to provide an example of an embodiment of each claimed invention. No embodiment described below limits any claimed invention and any claimed invention may cover apparatuses and methods that differ from those described below. The claimed inventions are not limited to apparatuses and methods having all of the features of any one apparatus or method described below, or to features common to multiple or all of the apparatuses or methods described below. It is possible that an apparatus or method described below is not an embodiment of any claimed invention. Any invention disclosed in an apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

When performing a cardiac catheterization using the radial artery for access, radiation exposure to the operating physician can be higher than during use of the femoral artery. In the context of increasing popularity of radial access, this greater radiation exposure for operating physicians performing cardiac catheterization is of concern, particularly given evidence suggesting a higher incidence of tumors among invasive cardiologists.

Current equipment, such as lead aprons and above-table shields, provide some protection, but it is desirable for operator radiation exposure to be reduced further, especially for cases using radial access. Existing cardiac catheterization labs can use non-specific arm support devices when gaining access to the radial artery. These devices can be clumsy, unprofessional, and uncomfortable for the patient and can provide little or no additional radiation protection. While more specific arm support devices have been created, they have many limitations, which can include: they can offer only modest, incremental radiation protection for the operating physician; they can increase patient and operator radiation dose and degrade the image quality due to the relative radiopacity and thickness of the materials used; and they can be inconvenient as they can require being removed between cases, or once the procedure begins, to avoid contaminating the sterile field.

The present disclosure relates to arm support apparatuses that are well suited for use in gaining access to a human patient's radial arteries during cardiac catheterization procedures.

Figure 1:
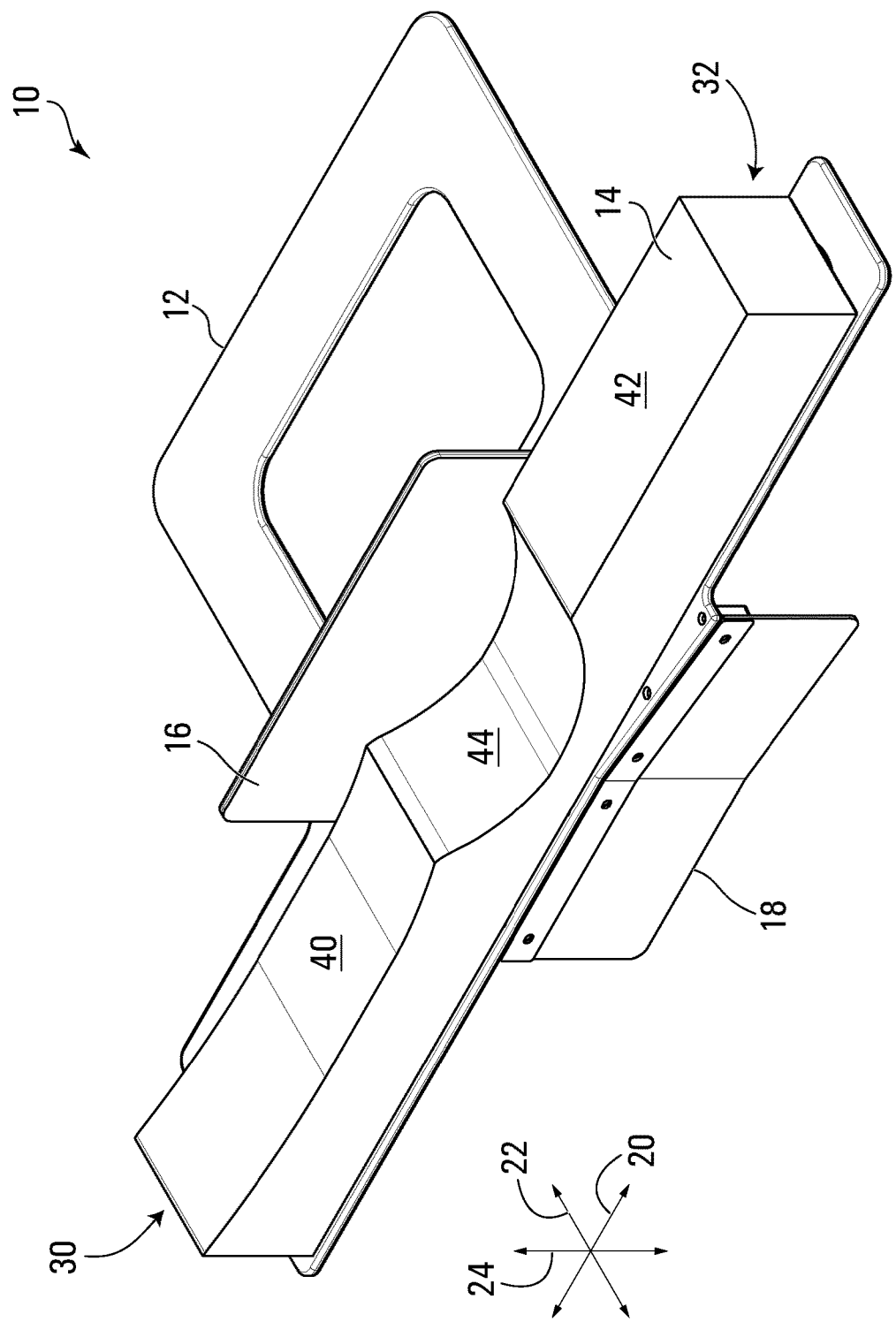
FIG. 1 is a perspective view of a first example of an arm support apparatus.
Figure 2:
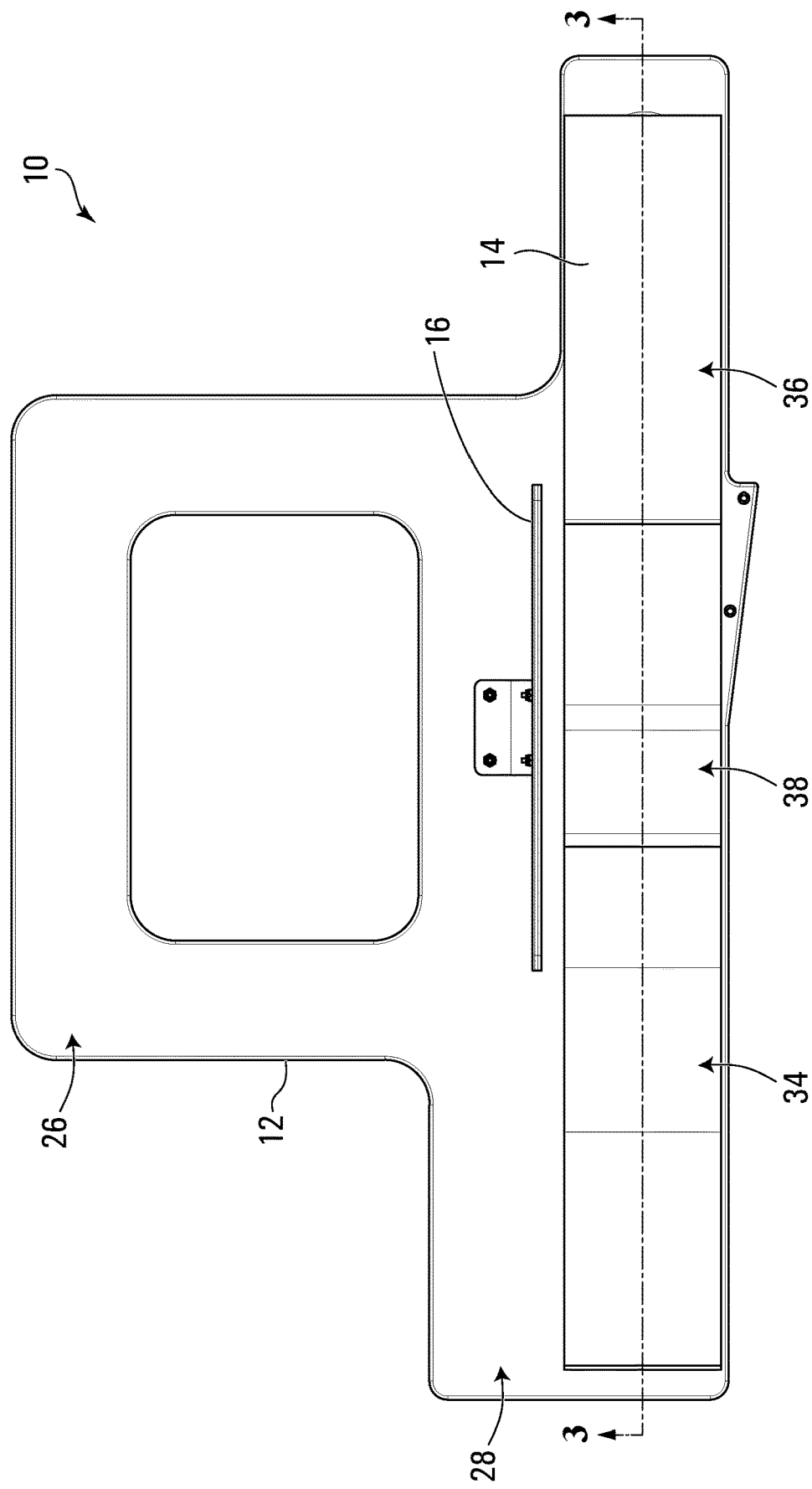
FIG. 2 is a top view of the apparatus of FIG. 1.

Referring to FIGS. 1 and 2, an example of an apparatus for supporting an arm of a human patient during a medical procedure is shown generally at reference number 10. The apparatus 10 as illustrated includes a base 12, and arm pad 14, a first barrier 16 and a second barrier 18. In use, the arm pad supports the right arm of the human patient, and the first and second barriers 16, 18 can shield an attending staff member from scatter radiation during the medical procedure.

In the example illustrated, the base 12 includes a medial portion 26 and a lateral portion 28. The medial portion 26 is configured to lie between the human patient and a table on which the human patient is supported. The lateral portion 28 extends in a lateral direction 22 from the medial portion 26.

To aid with understanding, FIG. 1 includes a directional legend, in which a longitudinal direction 20, the lateral direction 22, and a vertical direction 24 are shown.

In the example illustrated, the arm pad 14 is positioned on the lateral portion 28 of the base 12. The arm pad 14 extends in the longitudinal direction 20 between first and second ends 30, 32. In some examples, the arm pad 14 rests on the lateral portion 28, without being attached. This can allow adjustment of the position of the arm pad 14 according to patient's arm length. Therefore, the apparatus 10 can be customized to the patient's size without needing to move the patient or the base 12 underneath them. In other examples, the arm pad 14 can be fixed to the lateral portion 28.

In the example illustrated, the first barrier 16 is mounted to the base 12 and is positioned intermediate the medial and lateral portions 26, 28 in the lateral direction 22. The second barrier 18 is mounted to the lateral portion 28. The first barrier 16 extends upwardly from the base 12 in the vertical direction 24 to above the arm pad 14. The second barrier 18 extends downwardly from the base 12 in the vertical direction 24.

In the example illustrated, the arm pad 14 includes a proximal portion 34 adjacent to the first end 30, a distal portion 36 adjacent to the second end 32, and a central portion 38 arranged between the proximal and distal portions 34, 36. In use, the proximal portion 34 supports the arm of the human patient, and the central portion 38 supports a hand of the arm. The portions 34, 36, 38 each include an upper surface 40, 42, 44, respectively. In the example illustrated, each of the upper surfaces 40, 42, 44 is spaced above the lateral portion 28 of the base 12 in the vertical direction 24.

Referring to FIGS. 3 and 4, the lateral portion 28 of the base 12 extends in the longitudinal direction 20 to support a length of the arm pad 14. The first and second barriers 16, 18 are each shown arranged longitudinally intermediate of the arm pad 14. Furthermore, the central portion 38 of the arm pad 14 is shown arranged within a longitudinal extent of each of the first and second barriers 16, 18. With this arrangement, in use, the first and second barriers 16, 18 provide shielding of radiation in the vicinity of the hand of the human patient.

As shown in FIG. 3, the arm pad 14 can further include a radiopaque panel 46. In the example illustrated, the panel 46 is arranged in the central and distal portions 38, 36 of the arm pad 14, horizontally and adjacent to the lateral portion 28 of the base 12. In the example illustrated, the panel 46 can extend generally laterally between the first and second barriers 16, 18 to provide shielding of radiation in the vicinity of the hand of the human patient.

Figure 5:
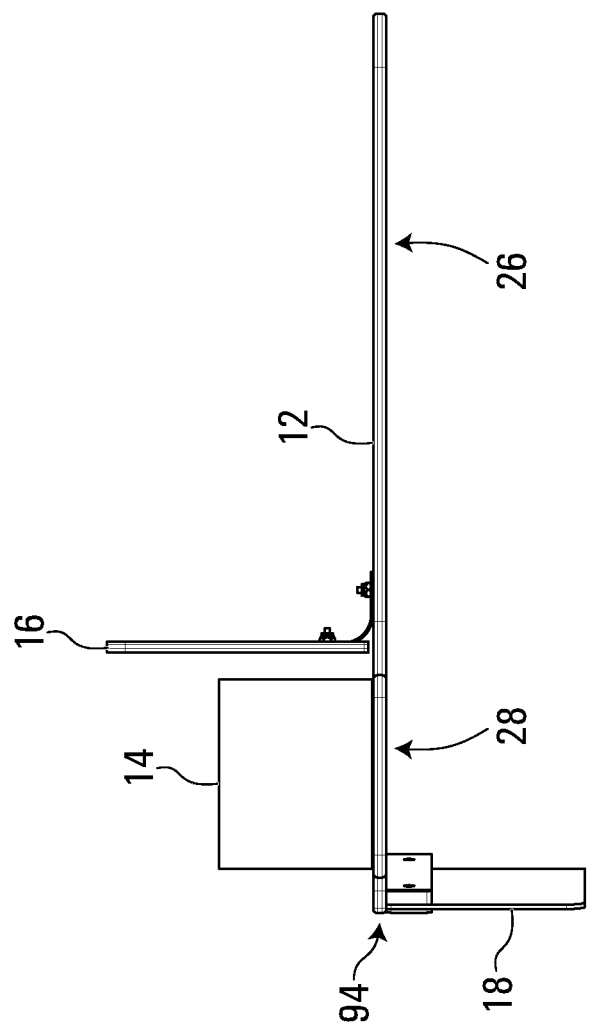
Figure 6:
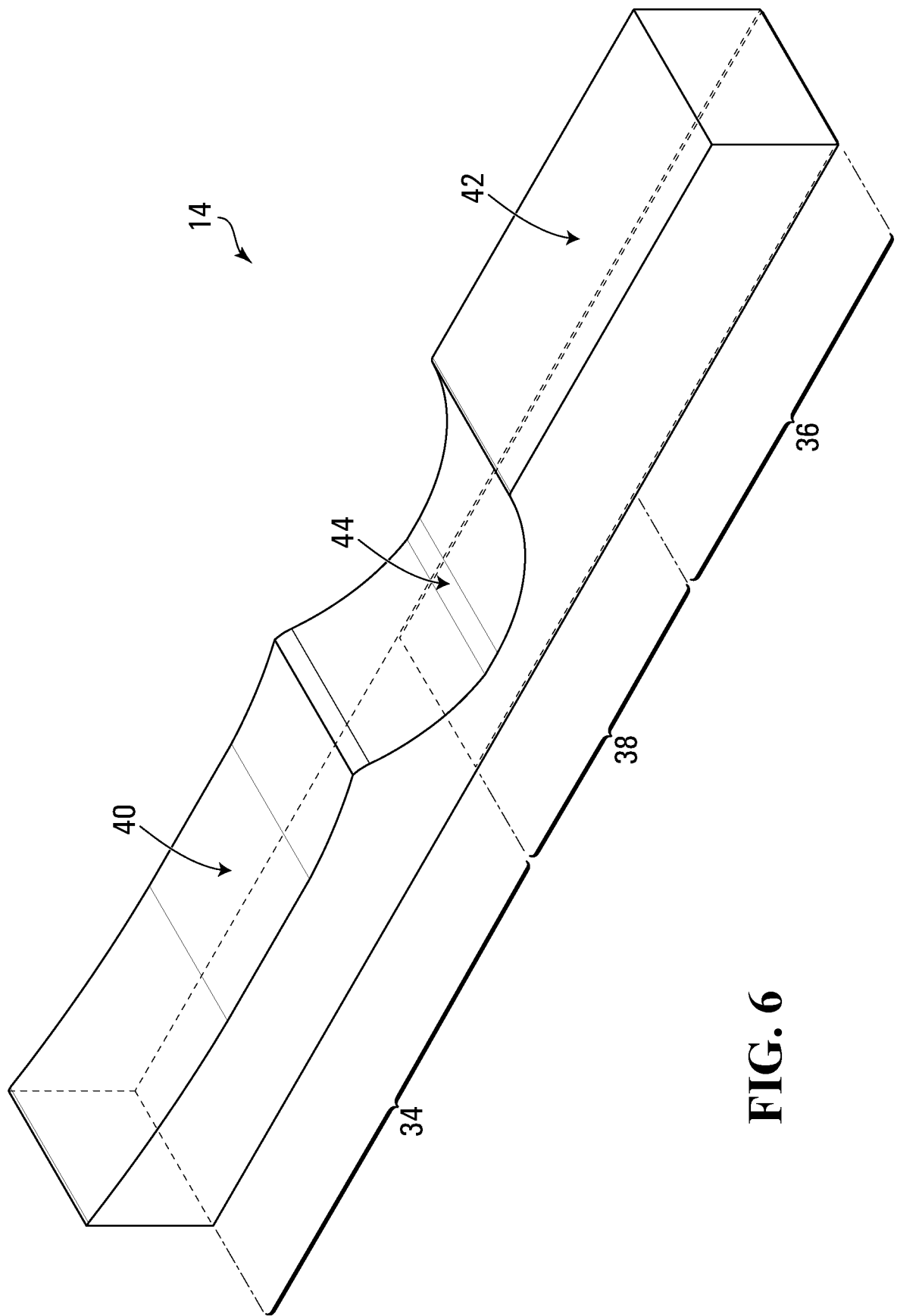
FIGS. 6, 7, 8 and 9 are perspective, side, bottom and end views, respectively, of an arm pad of the apparatus of FIG. 1.

Referring to FIG. 5, the lateral portion 28 of the base 12 extends laterally to support a width of the arm pad 14. In the example illustrated, the first barrier 16 is mounted to the base 12 and is positioned intermediate the medial and lateral portions 26, 28 in the lateral direction 22. The second barrier 18 is mounted to a lateral edge 94 of the lateral portion 28, and the arm pad 14 is positioned laterally intermediate the first and second barriers 16, 18.

Referring to FIGS. 6, 7, 8 and 9, it can be seen that the upper surface 44 of the central portion 38 is substantially below the upper surface 40 of the proximal portion 34. In the example illustrated, the upper surface 44 of the central portion 38 is concave in shape to position the hand generally below the arm. The upper surface 42 of the distal portion 36 is shown to be generally planar and horizontal, and can be used by the attending staff as a working surface.

Figure 7:
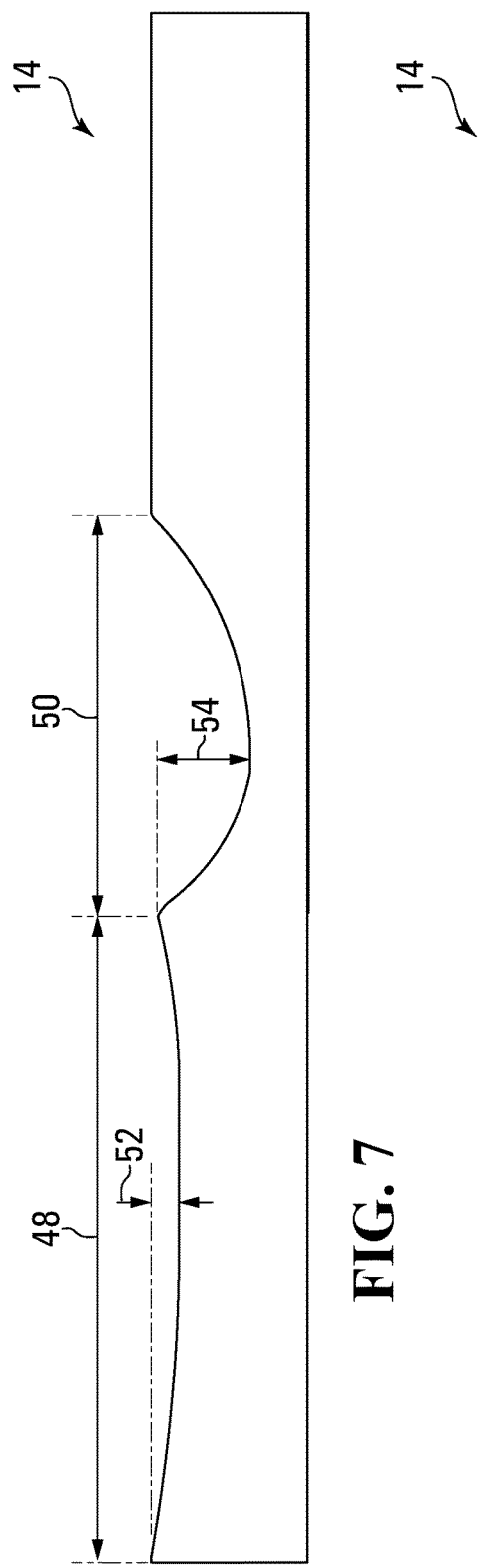
Figure 8:
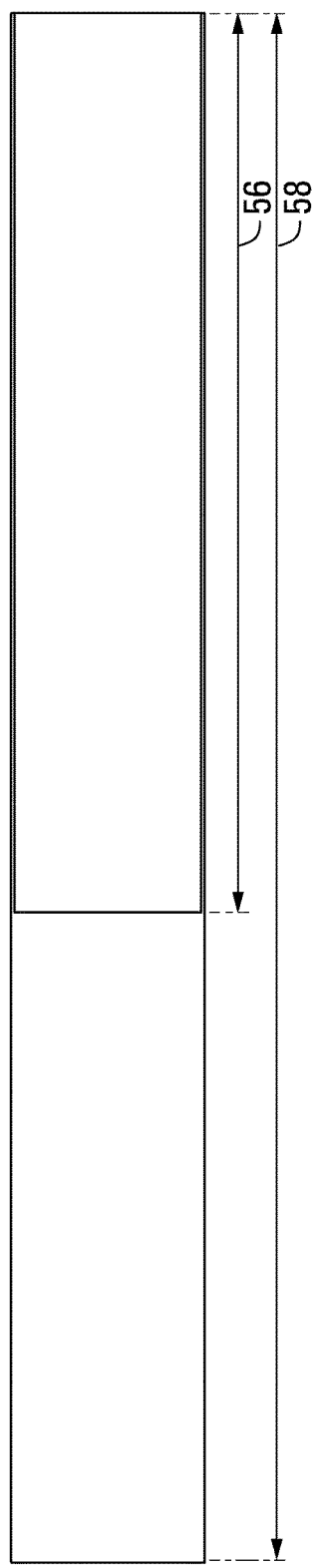
Figure 9:
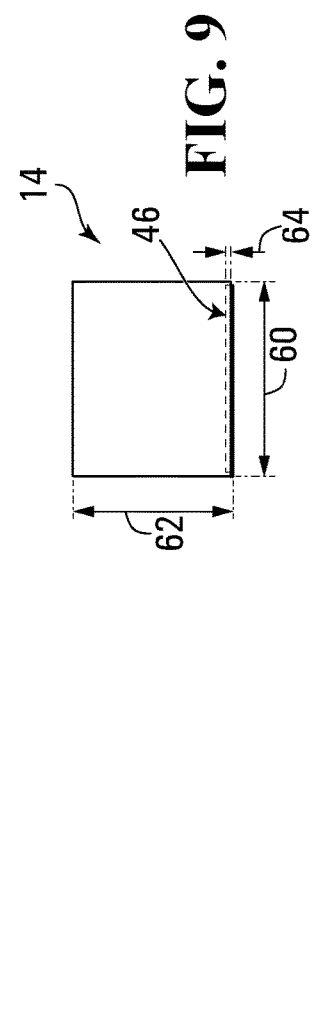

Dimensions for the arm pad 14 are shown in FIGS. 7, 8 and 9 and provided in Table 1. These dimensions are intended to be illustrative but non-limiting.

TABLE 1

| Dimension | Reference | mm |
| --- | --- | --- |
| Proximal portion length | 48 | 446 |
| Central portion length | 50 | 277 |
| Proximal portion drop | 52 | 19 |
| Central portion drop | 54 | 44 |
| Panel length | 56 | 619 |
| Overall length | 58 | 1067 |
| Overall width | 60 | 133 |
| Overall height | 62 | 76 |
| Panel height | 64 | 1 |

In some examples, the arm pad 14 can be formed of a foam material that is clad with marine grade vinyl. In some examples, the radiopaque panel 46 can be formed of a relatively thin layer of lead, which can be disposed in the arm pad 14 underneath a bottom outer vinyl layer. In some examples, the upper surface 42 of the distal portion 36 can be reinforced to create a stable working surface.

Figure 10:
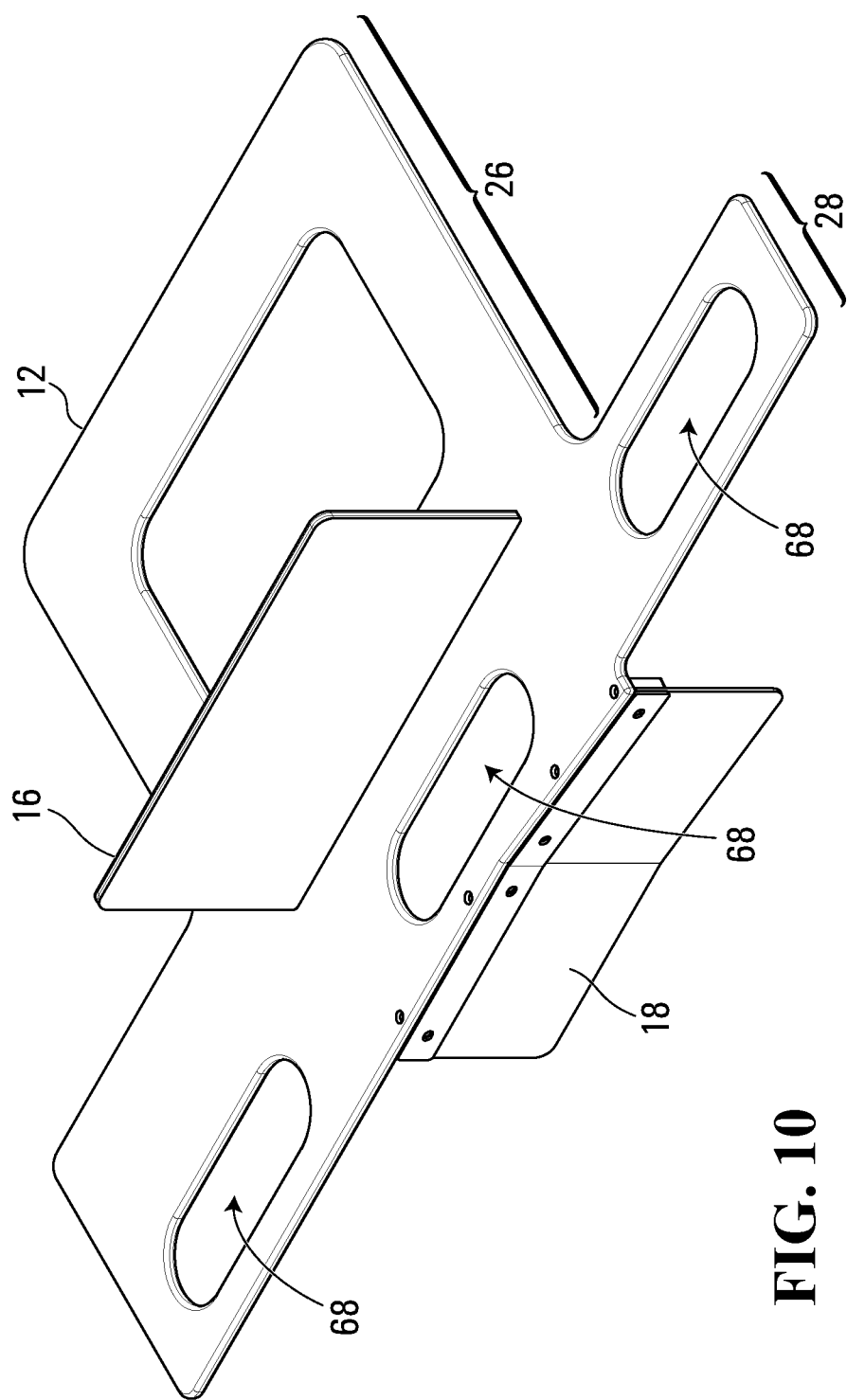
FIGS. 10, 11, 12, 13 and 14 are first and second perspective, top, side and end views, respectively, of the apparatus of FIG. 1, shown with the arm pad removed.
Figure 11:
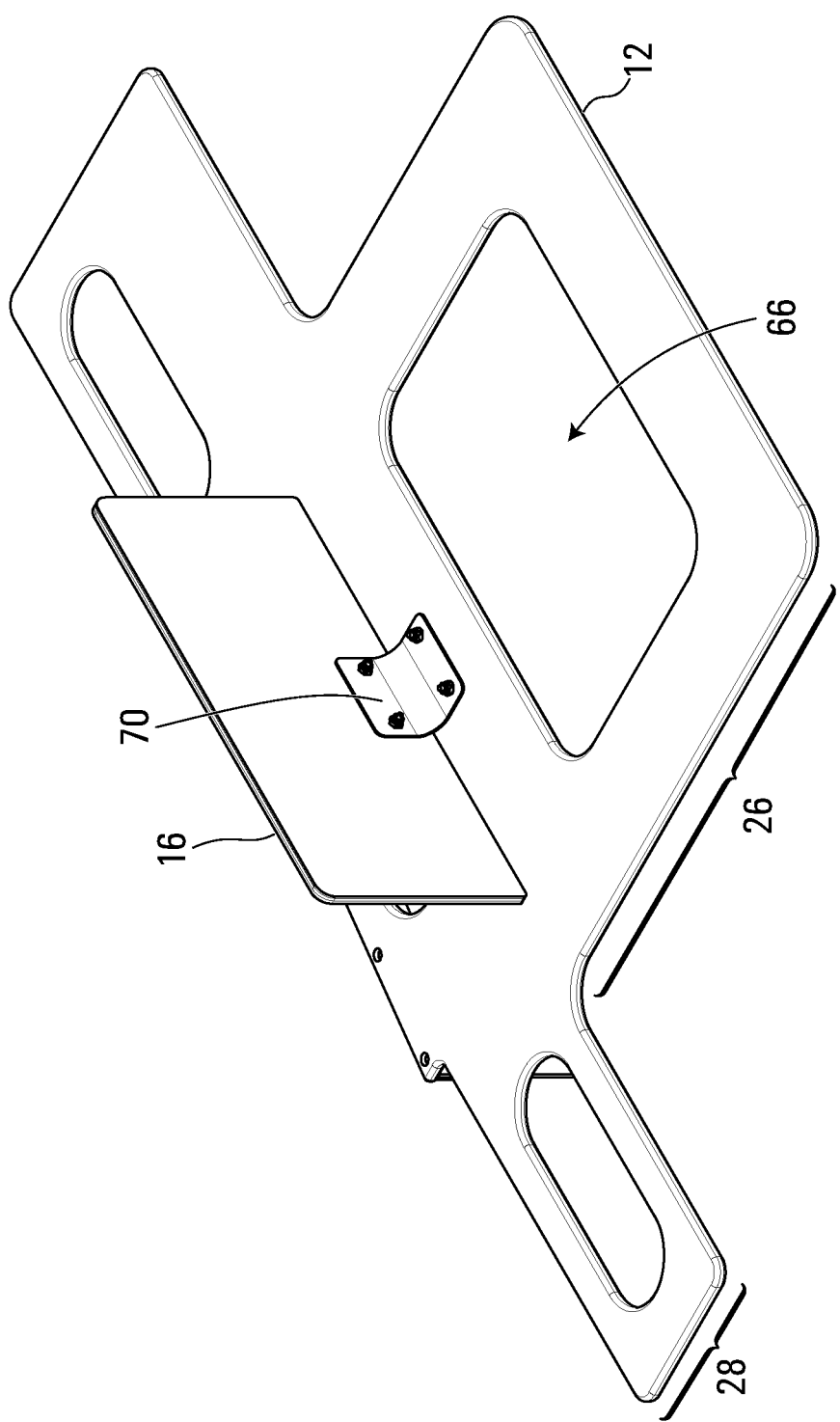
Figure 12:
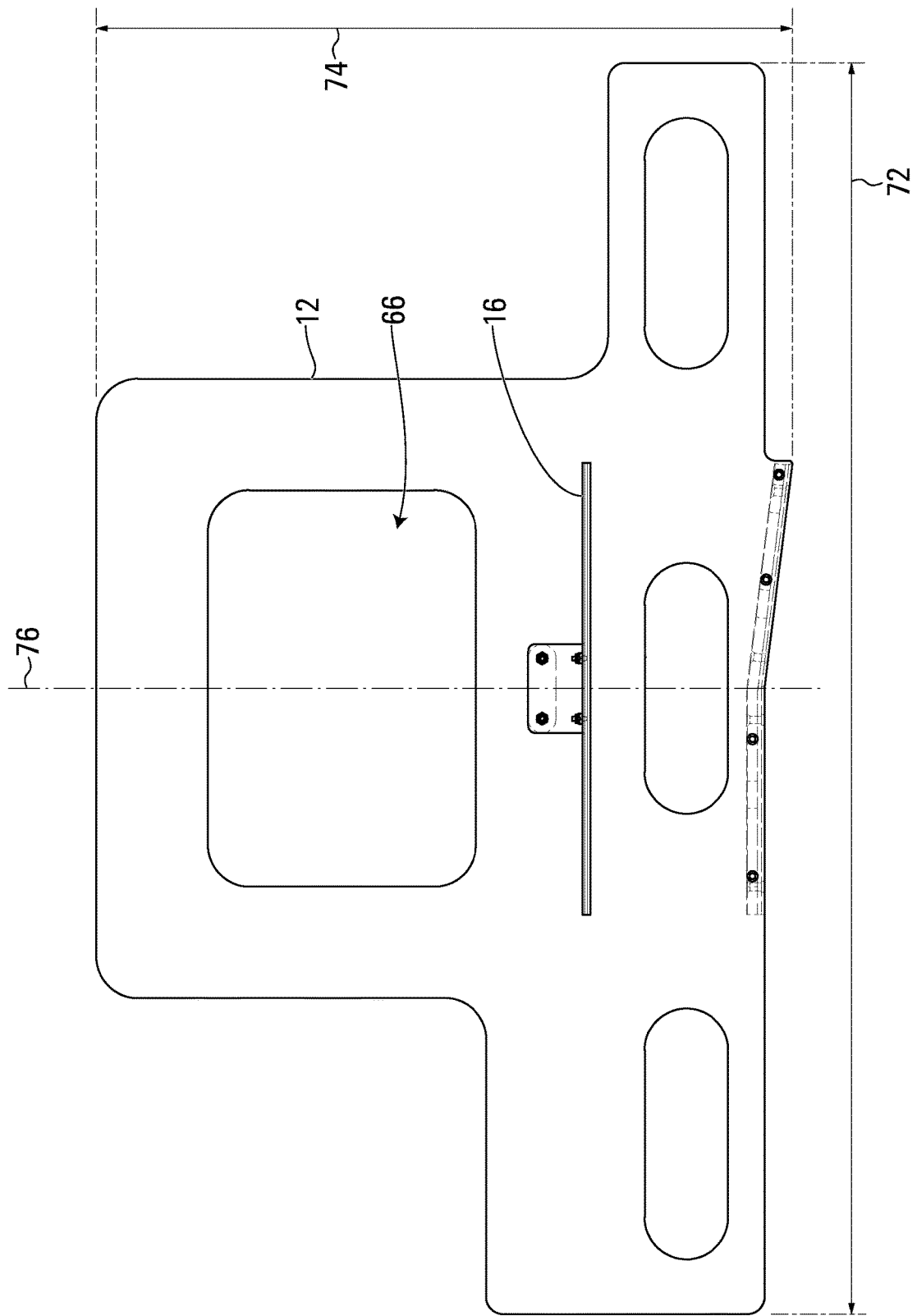

Referring to FIGS. 10, 11 and 12, the base 12 is shown to be generally planar and arranged horizontally. The base 12 can be formed at least partially of a substantially radiolucent material. In some examples, the base 12 can be formed of a unitary piece of clear polycarbonate material.

In the example illustrated, the medial portion 26 of the base 12 includes a central aperture 66 that is positioned so that, in use, it is underneath an abdomen of the human patient. The lateral portion 28 is also shown to include a series of apertures 68. The apertures 66, 68 can be cutouts of the base 12 that reduce weight and decrease impedance during medical imaging.

As shown in FIG. 11, the first barrier 16 can be mounted to the base 12 by a flexible and resilient connection 70 to permit adjustment of its position. In some examples, the connection 70 can be a curved bracket formed of spring steel, and fastened between the first barrier 16 and the base 12.

Dimensions for the base 12 are shown in FIG. 12 and provided in Table 2. These dimensions are intended to be illustrative but non-limiting.

TABLE 2

| Dimension | Reference | mm |
| --- | --- | --- |
| Base length | 72 | 1143 |
| Base width | 74 | 635 |

It can be seen in FIG. 12 that each of the aperture 66, the first barrier 16 and the second barrier 18 can be aligned with a transverse axis 76.

Figure 13:
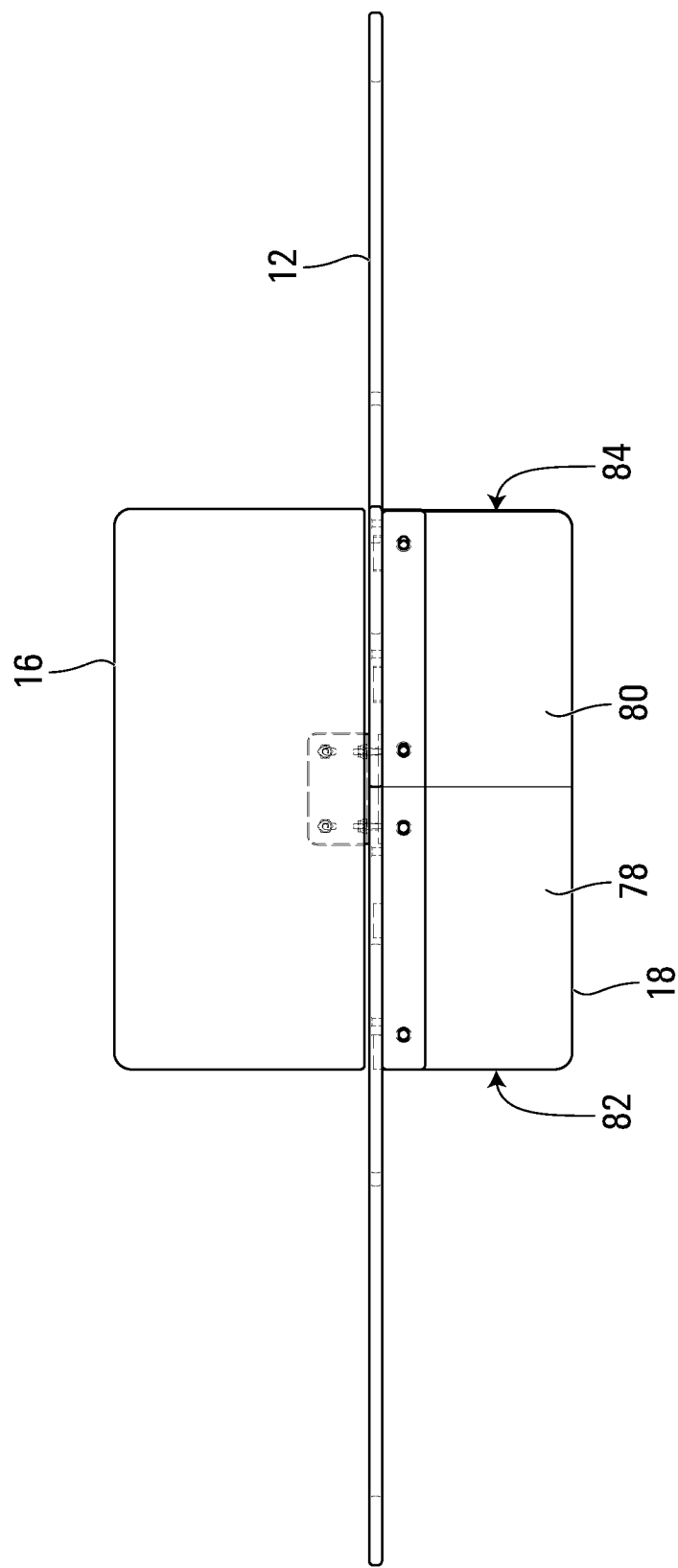
Figure 14:
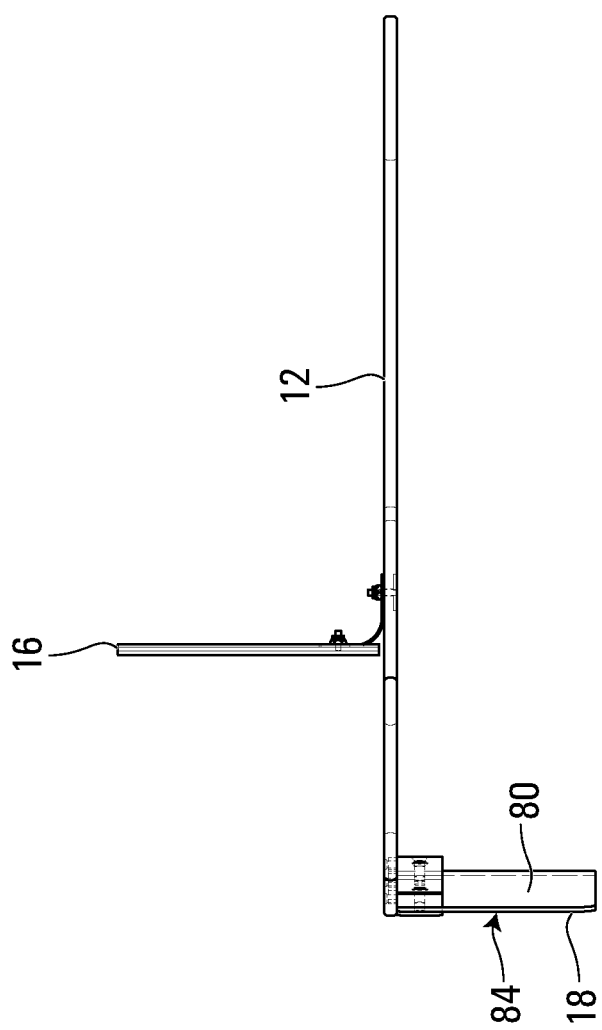

Referring to FIGS. 13 and 14, the first and second barriers 16, 18 are each shown to be generally planar and arranged vertically. The first and second barriers 16, 18 can each be formed at least partially of a substantially radiopaque material. In some examples, the first and second barriers 16, 18 can be formed of vinyl coated lead sheets.

In the example illustrated, the second barrier 18 includes first and second planar portions 78, 80. The planar portions 78, 80 have outward vertical edges 82, 84. In the example illustrated, the second planar portion 80 is joined to the first planar portion 78 at an oblique angle, so that the vertical edge 84 is spaced apart laterally from the vertical edge 82 in a direction away from the rest of the apparatus 10, which provides some clearance for a patient table.

Figure 15:
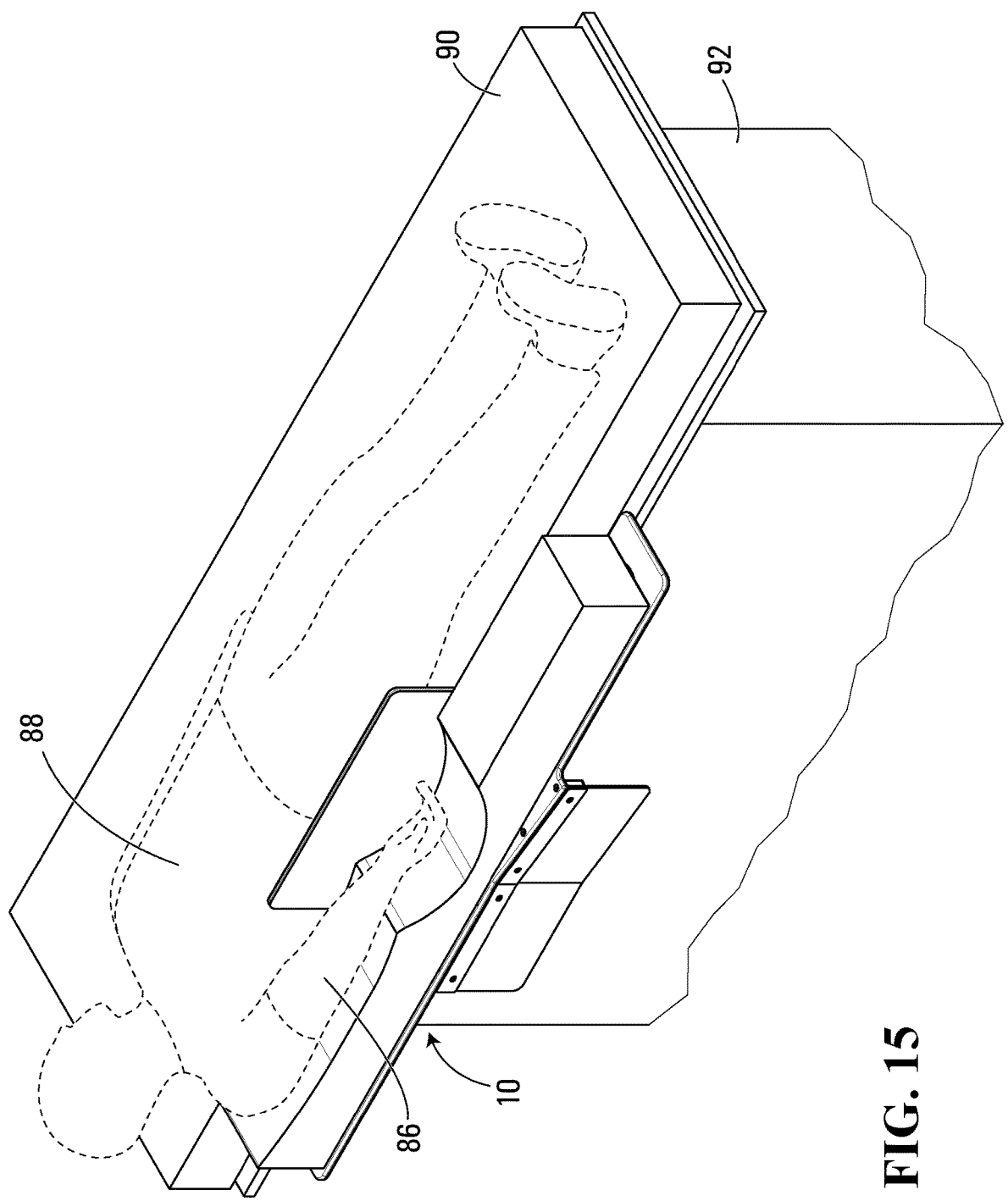
FIG. 15 is a perspective view of the apparatus of FIG. 1 and a human patient supported by a table.

Referring to FIG. 15, the apparatus 10 is shown supporting an arm 86 of a human patient 88. The human patient 88 is shown lying on a mattress 90 and a table 92.

In the example illustrated, the medial portion of the base lies between the human patient 88 and the table 92. It will be appreciated that, in other examples, the medial portion of the base can be omitted, and an alternative means of attaching the apparatus to the side of the table can be used.

There can be several advantages to the apparatus of the present disclosure over products currently on the market. These advantages relate to: increased radiation protection, improved visualization, greater operator convenience, and enhanced patient comfort.

In terms of increased radiation protection, the radiation barriers and panel can be substantially radiopaque, and can block significantly more radiation than existing shielding equipment. The apparatus can also be compatible with femoral access procedures, and provide radiation protection for such cases.

In terms of improved visualization, the polycarbonate base can be more radiolucent than existing devices, which can reduce the amount of radiation needed during medical imaging. Furthermore, the position of the base under the patient's abdomen is also outside of the typical field of view (the patient's chest), which can prevent both increases in radiation and image degradation. Moreover, the positioning of the radiation barriers and panel can allow clear fluoroscopic visualization of the patient's arm.

In terms of operator convenience, beyond the patient's hand, the working surface of the distal portion of the arm pad can be level with the patient's wrist and provide a convenient platform upon which the attending staff can manipulate equipment. Furthermore, the contoured shapes of the upper surfaces of the proximal and central portions of the arm pad can position the patient's wrist at a desirable angle, improving the attending staff's access to the patient's artery. Moreover, because the apparatus can be compatible with both radial and femoral access cases, the apparatus does not need to be removed between cases depending on the access site chosen.

Finally, the arm pad can be relatively large and include contoured foam padding to provide full arm support and enhance patient comfort. Furthermore, the flexibility of the first barrier allows for multiple positions to accommodate the patient, and because it is not rigidly attached it can deflect if it is knocked by the patient or the attending staff.

Figure 16:
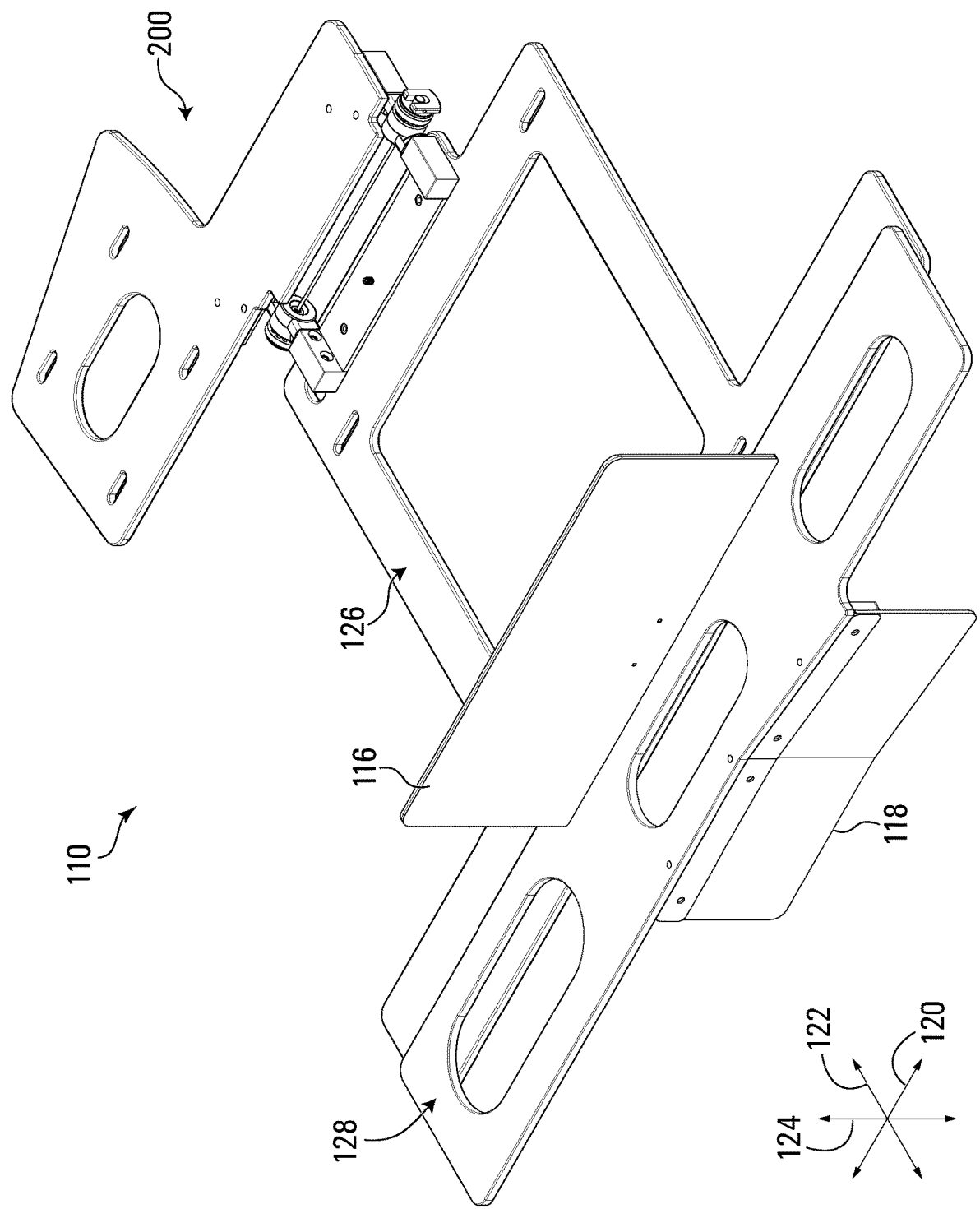
FIG. 16 is a perspective view of a second example of an arm support apparatus.
Figure 17:
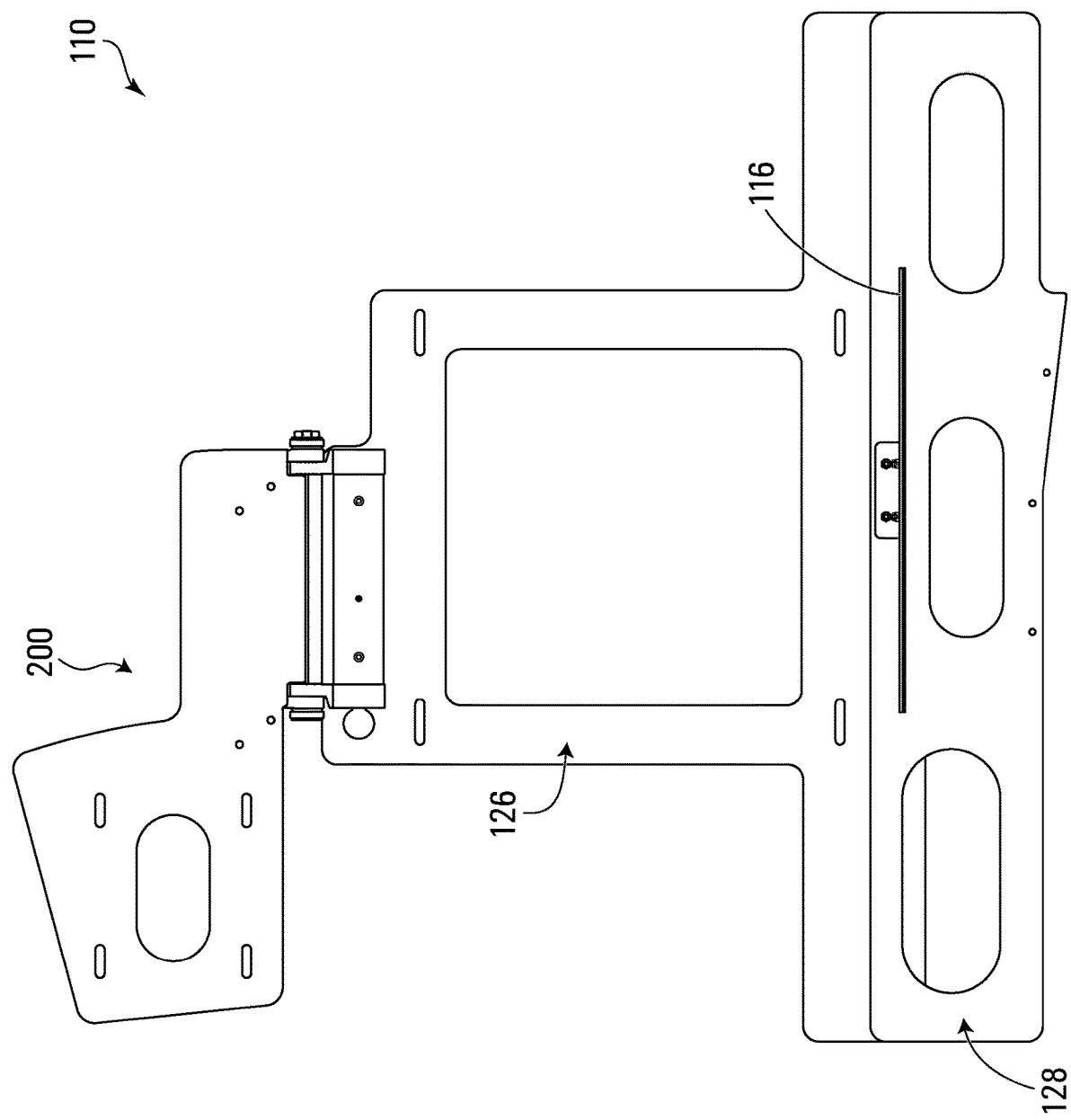
FIGS. 17 and 18 are top and end views, respectively, of the apparatus of FIG. 16.

Referring to FIGS. 16 and 17, another example of an apparatus for supporting an arm of a human patient during a medical procedure is shown generally at reference number 110. The apparatus 110 is shown to include a first barrier 116 and a second barrier 118. In use, the primary arm pad (omitted for clarity of illustration) supports the right arm of the human patient, and the first and second barriers 116, 118 can shield an attending staff member from scatter radiation during the medical procedure.

In the example illustrated, the apparatus 110 includes a base that includes a medial portion 126 and a lateral portion 128. The medial portion 126 is configured to lie between the human patient and a table on which the human patient is supported. The lateral portion 128 extends in a lateral direction 122 from the medial portion 126. To aid with understanding, a longitudinal direction 120, the lateral direction 122, and a vertical direction 124 are shown in FIG. 16.

In the example illustrated, the first and second barriers 116, 118 are each mounted to the lateral portion 128 and are spaced from one another in the lateral direction 122. The first barrier 116 extends upwardly in the vertical direction 124, and the second barrier 118 extends downwardly in the vertical direction 124.

In the example illustrated, the apparatus 110 includes an additional support surface that is shown generally at reference numeral 200, which can be referred to as the "left wing". The left wing 200 is shown coupled to the medial portion 126 opposite from the lateral portion 128, and extends in the lateral direction 122 away from the medial portion 126. In use, the left wing 200 can support the left arm of the human patient.

Figure 18:
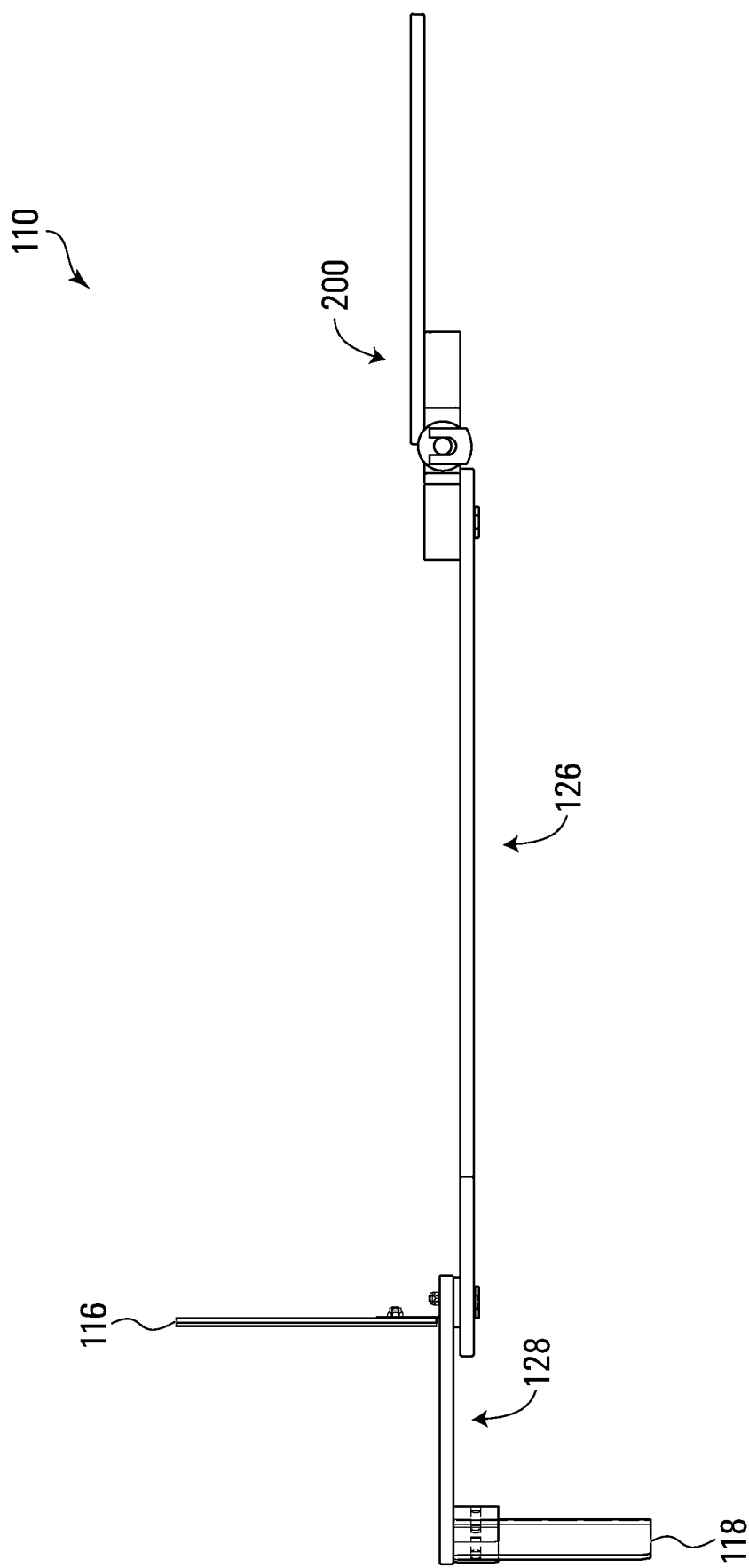

Referring to FIG. 18, the lateral portion 128 extends laterally to support a width of the primary arm pad (not shown). In the example illustrated, the first barrier 116 is mounted adjacent to a first lateral edge of the lateral portion 128, and the second barrier 118 is mounted to a second lateral edge of the lateral portion 128.

In the example illustrated, the medial and lateral portions 126, 128 of the base are separate components that are capable of disassembly. The medial portion 126 is arranged laterally intermediate the lateral portion 128 and the left wing 200.

Figure 19:
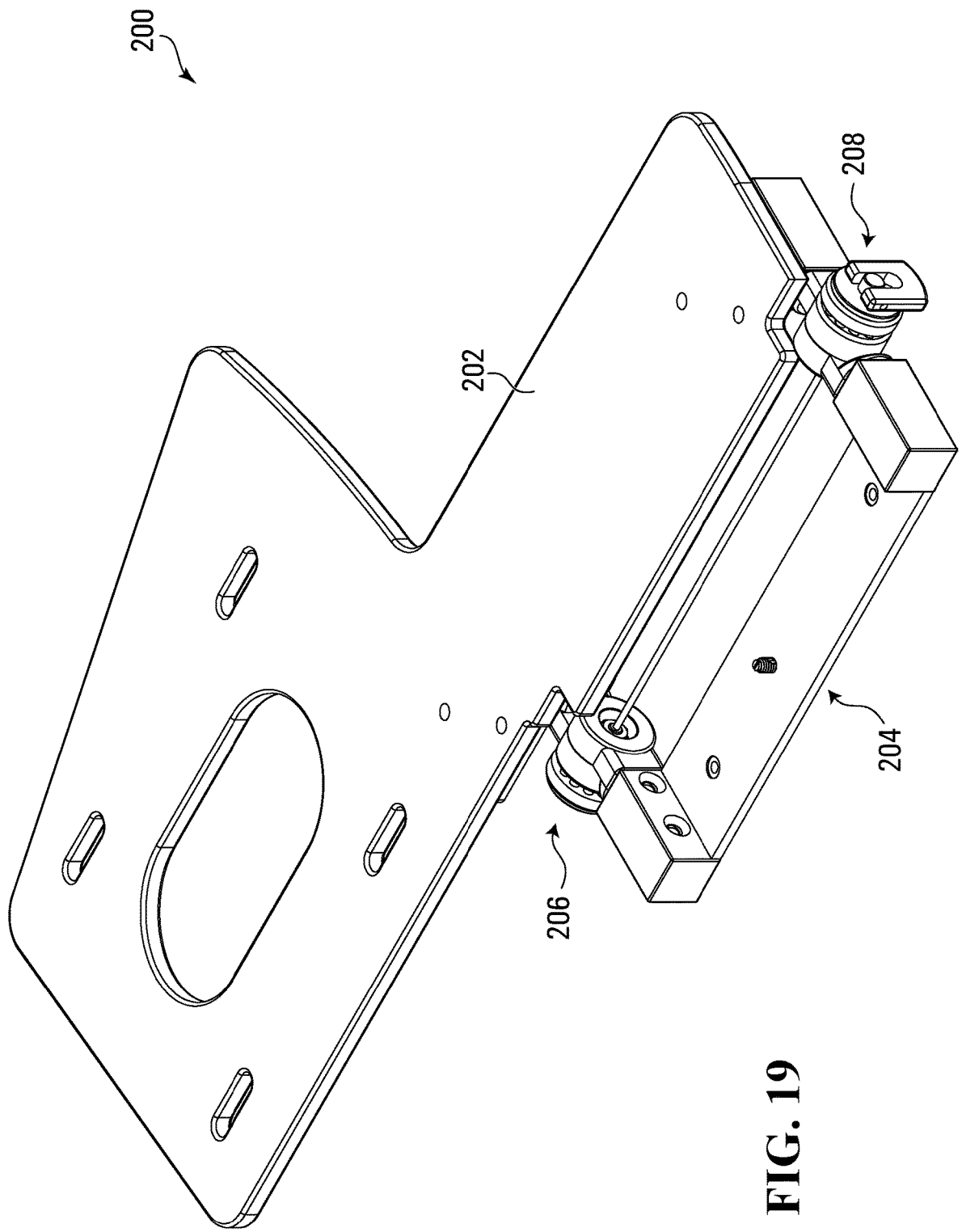
FIG. 19 is a perspective view of a left wing of the apparatus of FIG. 16.

Referring to FIG. 19, the left wing 200 is shown to include an adjustable support 202 that is coupled to a mounting bracket 204 by hinge mechanisms 206, 208. The support 202 is shown to be generally planar and includes a plurality of cutouts. In the example illustrated, the support 202 includes a central cutout, intended to reduce weight, and four peripheral cutouts, which are designed to accept straps to secure a secondary arm pad (not shown) to the support 202. In the example illustrated, the support 202 has a relatively large upper portion, and a relatively narrow lower portion adjacent to the hinge mechanisms 206, 208, and is therefore shaped to be less intrusive when pivoted upwardly towards the patient.

Figure 20:
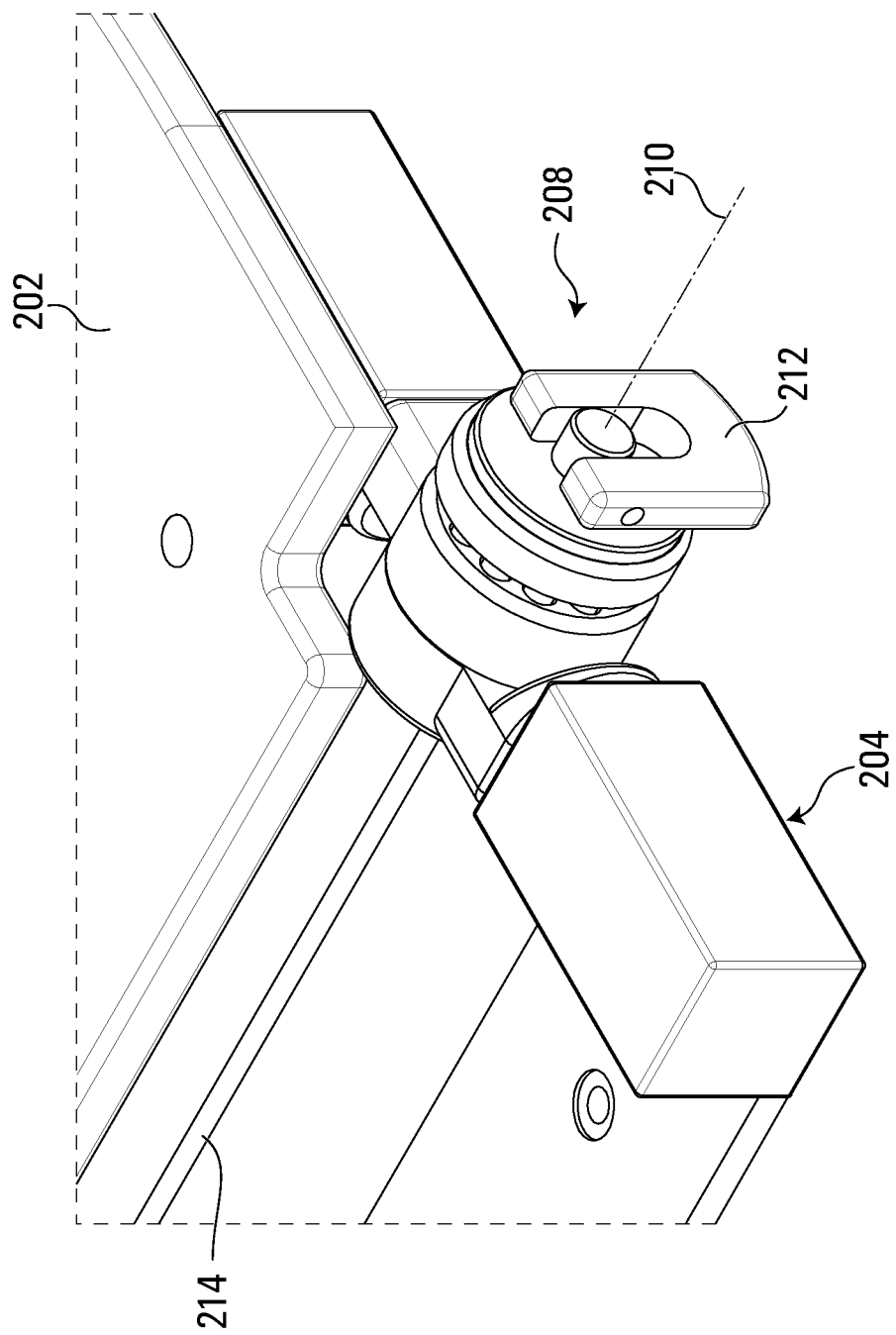
FIG. 20 is a detailed view of a portion of FIG. 19.

Referring to FIG. 20, the support 202 can be pivoted about a longitudinal axis 210 by actuating a tab 212. The tab 212 disengages locks in the hinge mechanisms 206, 208 to permit pivoting of the support 202 about the axis 210. Releasing the tab 212 reengages the locks to fix the support 202 at a desired angle. In the example illustrated, the tab 212 is provided at the hinge mechanism 208, and coordination between the hinge mechanisms 206, 208 can be achieved via a shaft 214. This can allow for one handed adjustment of the left wing 200.

Figure 21:
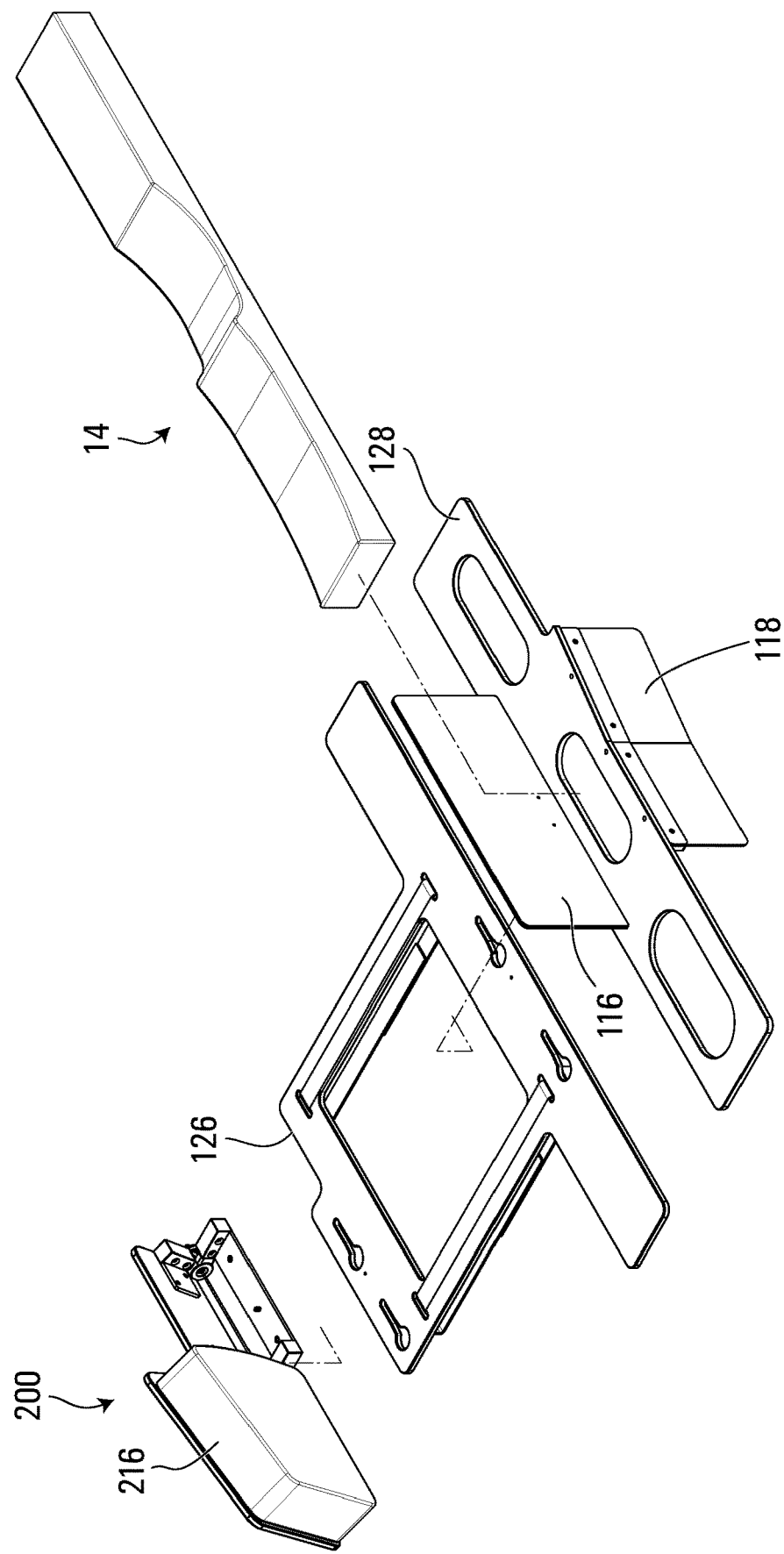
FIG. 21 is an exploded view of the apparatus of FIG. 16 in combination with arm pads.

FIG. 21 shows disassembly of the lateral portion 128 and the left wing 200 from the medial portion 126. In the example illustrated, the lateral portion 128 and the left wing 200 each includes pins that are arranged to engage keyhole slots in the medial portion 126, permitting quick and easy assembly/disassembly.

In the example illustrated, the primary arm pad 14 can rest on the lateral portion 128, and the secondary arm pad 216 is fixed to the left wing 200 by straps. Two straps are also shown attached to the medial portion 126, for securing the medial portion 126 to a mattress (not shown)

Figure 22:
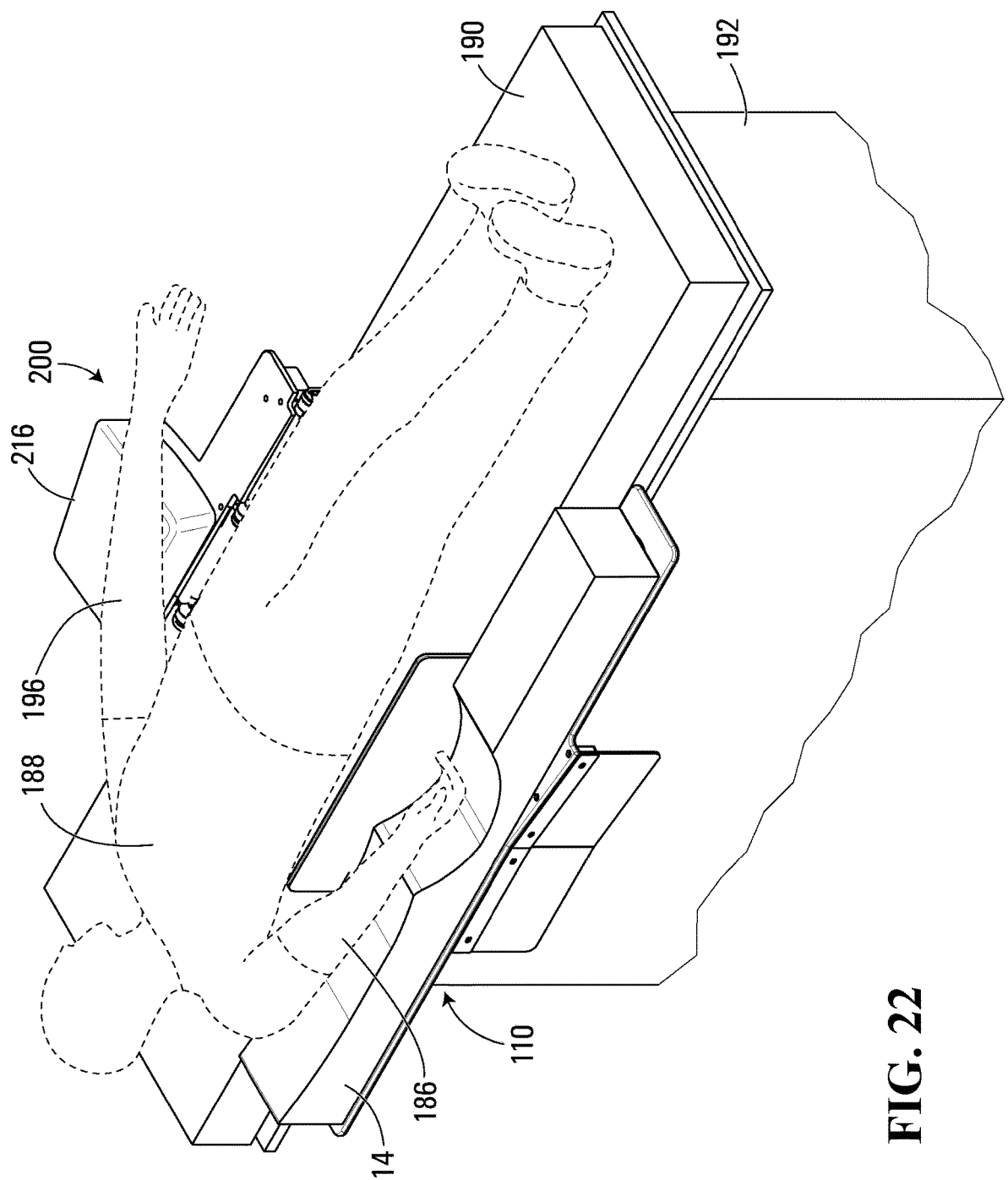
FIGS. 22 and 23 are perspective views of the apparatus of FIG. 16, the arm pads and a human patient supported by a table.
Figure 23:
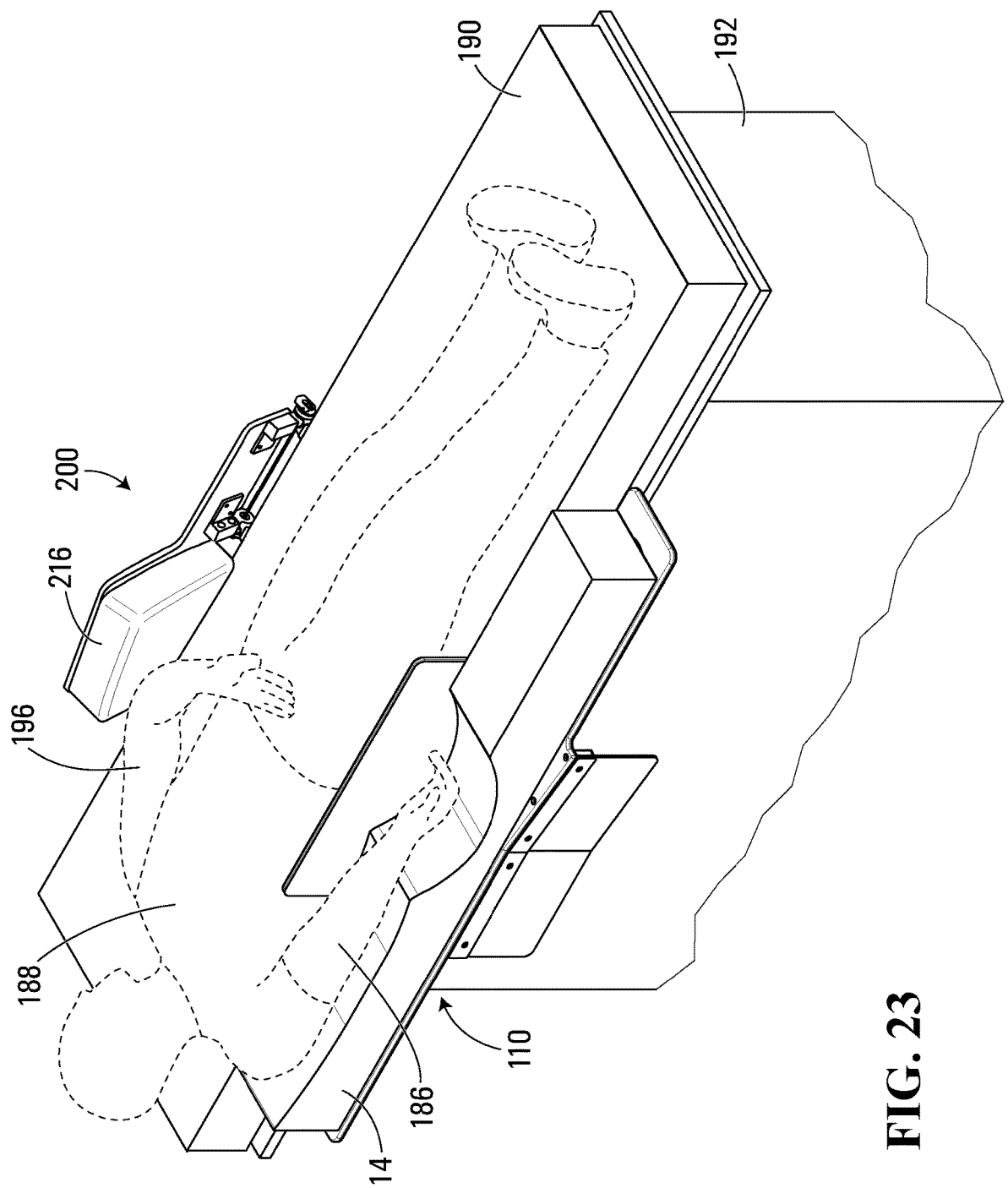

Referring to FIGS. 22 and 23, the apparatus 110 is shown supporting arms 186, 196 of a human patient 188 lying on a mattress 190 and a table 192.

FIG. 22 shows the arm pad 216 and the left wing 200 in a generally horizontal position. In use, the arm pad 216 can support the left arm 196 of the human patient 188 during a medical procedure, in which the left radial artery of the human patient 188 can be accessed, for example. During the medical procedure, the attending staff member can remain along the right hand side relative to the human patient 188, and the apparatus 110 can therefore continue to shield the attending staff member from scatter radiation.

FIG. 23 shows the left wing 200 in an upright position in which there is an acute angle between the support 202 and the medial portion 126. This can be a more comfortable position for the human patient 188 to maintain, after the left radial artery has been accessed, and during which images can be taken using a C-arm camera, for example.

It will be appreciated that the subject matter of interest herein is not necessarily limited to implementation in cardiac catheterization labs, and can apply more broadly to other medical procedures.

Furthermore, it will be appreciated that terms used herein to convey geometrical or mathematical relationships need not be construed with absolute precision. For example, the terms 'concave' and 'convex' as used herein need not be interpreted to mean structures having a curved surface that is exactly circular. These terms and other terms herein may be interpreted with some flexibility, without strict adherence to mathematical definitions, as will be appreciated by persons skilled in the art. It will also be appreciated that terms used herein to connote orientation, including 'up', 'down', 'above', 'below', 'lateral', 'longitudinal', 'vertical' and 'horizontal', correspond to the arm board apparatus in use and are intended to aid with understanding, but need not refer to the orientation of various components during manufacture or when not in use.

While the above description provides examples of one or more apparatuses or methods, it will be appreciated that other apparatuses or methods may be within the scope of the accompanying claims.

We claim:

1. An apparatus for supporting an arm of a human patient during a medical procedure, the apparatus comprising: a base comprising a medial portion that is configured to lie between the human patient and a table on which the human patient is supported, and a lateral portion that extends laterally from the medial portion; an arm pad positioned on the lateral portion of the base, the arm pad extending longitudinally between first and second ends; a first barrier for shielding scatter radiation during the medical procedure, the first barrier mounted to the base and positioned laterally intermediate the medial and lateral portions thereof; and a second barrier for shielding scatter radiation during the medical procedure, the second barrier mounted to the lateral portion of the base and extending downwardly therefrom, wherein the arm pad comprises a proximal portion adjacent to the first end for supporting the arm of the human patient, a distal portion adjacent to the second end, a central portion arranged between the proximal and distal portions for supporting a hand of the arm, and a radiopaque panel for shielding scatter radiation during the medical procedure in the vicinity of the hand of the human patient, wherein an upper surface of the proximal portion is spaced above the lateral portion of the base, an upper surface of the central portion is spaced above the lateral portion of the base, and the upper surface of the central portion is substantially below the upper surface of the proximal portion, and wherein the first barrier extends upwardly from the base to a height above both the proximal and central upper surfaces of the arm pad.

2. The apparatus of claim 1, wherein the upper surface of the central portion is concave in shape to position the hand generally below the arm.

3. The apparatus of claim 1, wherein the first barrier is arranged longitudinally intermediate of the arm pad, the second barrier is arranged longitudinally intermediate of the arm pad, the central portion of the arm pad is arranged within a longitudinal extent of the first barrier, the central portion of the arm pad is arranged within a longitudinal extent of the second barrier, and the distal portion comprises an upper surface that is generally planar and horizontal.

4. The apparatus of claim 1, wherein the radiopaque panel is arranged in the central and distal portions of the arm pad, and the radiopaque panel is arranged horizontally and adjacent to the base.

5. The apparatus of claim 1, wherein the base is generally planar and formed at least partially of a substantially radiolucent material.

6. The apparatus of claim 5, wherein the medial portion of the base comprises a central aperture that is configured to be positioned underneath an abdomen of the human patient.

7. The apparatus of claim 5, wherein the lateral portion of the base extends longitudinally to support a length of the arm pad, and the lateral portion of the base extends laterally to support a width of the arm pad.

8. The apparatus of claim 7, wherein the arm pad is detached from the base.

9. The apparatus of claim 1, wherein the first and second barriers are each generally planar and formed at least partially of a substantially radiopaque material, and the first and second barriers are each arranged generally vertically.

10. The apparatus of claim 9, wherein the first barrier is mounted to the base by a flexible and resilient connection to permit manual adjustment of its position.

11. The apparatus of claim 9, wherein the second barrier is mounted to a lateral edge of the lateral portion, and the arm pad is positioned laterally intermediate the first and second barriers.

12. The apparatus of claim 11, wherein the second barrier has a first vertical edge that is closer to the first end of the arm pad and a second vertical edge that is closer to the second end of the arm pad, and the second vertical edge is spaced apart laterally from the first vertical edge in a direction away from the arm pad.

13. The apparatus of claim 12, wherein the second barrier comprises first and second planar portions that define the first and second vertical edges, respectively, and the second planar portion is joined to the first planar portion at an oblique angle.

14. The apparatus of claim 1, comprising a left wing that extends laterally from the medial portion opposite from the lateral portion, the left wing comprising an adjustable support that is configured to support the left arm of the human patient.

15. The apparatus of claim 14, wherein the support is pivotable about a longitudinal axis between a generally horizontal position and an upright position in which there is an acute angle between the support and the medial portion.

16. The apparatus of claim 15, comprising at least one hinge mechanism coupling the medial portion and the support that is configured to adjust the angle between the support and the medial portion.

17. An apparatus, comprising: a base; a first barrier mounted to the base for shielding scatter radiation, the first barrier extending upwardly from the base; a second barrier mounted to the base for shielding scatter radiation, the second barrier extending downwardly from the base; and an arm pad on the base positioned laterally intermediate the first and second barriers, the arm pad comprising a proximal portion for supporting an arm of a human patient, a central portion for supporting a hand of the arm and having an upper surface being substantially below an upper surface of the proximal portion, and a radiopaque panel for shielding scatter radiation in the vicinity of the hand of the human patient, wherein the first barrier extends upwardly from the base to a height above both the proximal and central upper surfaces of the arm pad.

18. The apparatus of claim 17, wherein the upper surface of the central portion is concave in shape to position the hand generally below the arm.

19. The apparatus of claim 18, wherein the radiopaque panel is arranged in the central portion of the arm pad, and the radiopaque panel is arranged horizontally and adjacent to the base.

20. A method of supporting an arm of a human patient, the method comprising: positioning a base to lie between the human patient and a table on which the human patient is supported, the base comprising a lateral portion that extends laterally from the table; placing the arm of the human patient on an arm pad that is positioned on the lateral portion of the base, the arm pad comprising a proximal portion comprising an upper surface for supporting the arm of the human patient, a central portion comprising an upper surface for supporting a hand of the arm being generally below the arm, and a radiopaque panel; shielding scatter radiation with the radiopaque panel in the vicinity of the hand of the human patient; shielding scatter radiation with a first barrier, the first barrier mounted to the base and positioned laterally intermediate the lateral portion and the human patient, the first barrier extending upwardly from the base to a height above both the proximal and central upper surfaces of the arm pad; and shielding scatter radiation with a second barrier, the second barrier mounted to the lateral portion of the base and extending downwardly therefrom.

* * * * *